(12) United States Patent
Lee et al.

(10) Patent No.: US 6,183,481 B1
(45) Date of Patent: Feb. 6, 2001

(54) DELIVERY SYSTEM FOR SELF-EXPANDING STENTS AND GRAFTS

(75) Inventors: Peter Y. Lee, Canton, OH (US); William M. Colone, Phoenix, AZ (US); Barbara L. Teeter, Phoenix, AZ (US); William L. Creer, Phoenix, AZ (US); Kevin G. Farl, Phoenix, AZ (US)

(73) Assignee: Endomed Inc., Phoenix, AZ (US)

( * ) Notice: Under 35 U.S.C. 154(b), the term of this patent shall be extended for 0 days.

(21) Appl. No.: 09/401,599

(22) Filed: Sep. 22, 1999

(51) Int. Cl.$^7$ .................................................. A61B 19/00
(52) U.S. Cl. ........................ 606/108; 606/151; 606/191; 623/1.11
(58) Field of Search .................................... 606/108, 151, 606/190, 191, 192, 193, 194, 195, 196, 187, 198; 623/1.11

(56) References Cited

U.S. PATENT DOCUMENTS

| | | |
|---|---|---|
| 3,657,744 | 4/1972 | Ersek . |
| 3,953,566 | 4/1976 | Gore . |
| 4,140,126 | 2/1979 | Choudhury . |
| 4,187,390 | 2/1980 | Gore . |
| 4,482,516 | 11/1984 | Bowman et al. . |
| 4,544,711 | 10/1985 | Mancinelli . |
| 4,580,568 | 4/1986 | Gianturco . |
| 4,617,932 | 10/1986 | Kornberg . |
| 4,655,771 | 4/1987 | Wallsten . |
| 4,800,882 | 1/1989 | Gianturco . |
| 4,907,336 | 3/1990 | Gianturco . |
| 4,955,899 | 9/1990 | Della Corna et al. . |
| 5,019,085 * | 5/1991 | Hillstead ................ 606/108 |
| 5,122,154 | 6/1992 | Rhodes . |
| 5,123,917 | 6/1992 | Lee . |
| 5,152,782 | 10/1992 | Kowligi et al. . |
| 5,302,317 | 4/1994 | Boller et al. . |
| 5,316,023 | 5/1994 | Palmaz et al. . |
| 5,415,664 * | 5/1995 | Pinchhk ................ 606/108 |
| 5,484,444 * | 1/1996 | Braunschweiler et al. ........ 606/108 |
| 5,489,295 | 2/1996 | Piplani et al. . |
| 5,507,767 | 4/1996 | Maeda et al. . |
| 5,507,771 | 4/1996 | Gianturco . |
| 5,575,816 | 11/1996 | Rudnick et al. . |
| 5,609,627 | 3/1997 | Goicoechea et al. . |
| 5,632,763 | 5/1997 | Glastra . |
| 5,639,278 | 6/1997 | Dereume et al. . |
| 5,662,713 | 9/1997 | Andersen et al. . |
| 5,695,517 | 12/1997 | Marin et al. . |

(List continued on next page.)

FOREIGN PATENT DOCUMENTS

| | | |
|---|---|---|
| 0893108A2 | 1/1999 | (EP) . |
| WO92/19310 | 11/1992 | (WO) . |
| WO95/05555 | 2/1995 | (WO) . |
| WO98/26731 | 6/1998 | (WO) . |
| WO98/31306 | 7/1998 | (WO) . |
| WO98/00090 | 8/1998 | (WO) . |
| WO98/36708 | 8/1998 | (WO) . |
| WO98/38947 | 11/1998 | (WO) . |

OTHER PUBLICATIONS

Alexis Carrel, "Results of the permanent intubation of the thoracic aorta", Surgery, Gynecology and Obstetrics, vol. XV, No. 3, Sep. 1912 pp. 245–248.

Primary Examiner—Pedro Philogene
(74) Attorney, Agent, or Firm—David E. Rogers; Michael A. Lechter; Squire, Sanders & Dempsey

(57) ABSTRACT

A device for disposing a radially self-expanding endoprosthesis in a body lumen. The implantation device includes an elongated catheter having a distal end and an outer surface over which the endoprosthesis is placed a sheath disposed to releasably surround at least a portion of the endoprosthesis, holding the endoprosthesis on the catheter in a radially contracted state, and a flexible elongation release element cooperating with the sheath. The sheath is released, permitting the surrounded portion of the endoprosthesis to expand, by axial withdrawal of the release element.

23 Claims, 12 Drawing Sheets

U.S. PATENT DOCUMENTS

| | | |
|---|---|---|
| 5,700,269 | 12/1997 | Pinchuk et al. . |
| 5,700,285 | 12/1997 | Myers et al. . |
| 5,718,724 | 2/1998 | Goicoechea et al. . |
| 5,749,880 | 5/1998 | Banas et al. . |
| 5,755,734 | 5/1998 | Richter et al. . |
| 5,776,142 | 7/1998 | Gunderson . |
| 5,824,037 | 10/1998 | Fogarty et al. . |
| 5,827,320 | 10/1998 | Richter et al. . |
| 5,833,694 | 11/1998 | Poncet . |
| 5,873,906 | 2/1999 | Lau et al. . |
| 5,906,640 | 5/1999 | Penn et al. . |
| 5,906,641 | 5/1999 | Thompson et al. . |
| 5,916,263 | 6/1999 | Goicoechea et al. . |
| 6,027,510 * | 2/2000 | Alt ........................................ 606/108 |

* cited by examiner

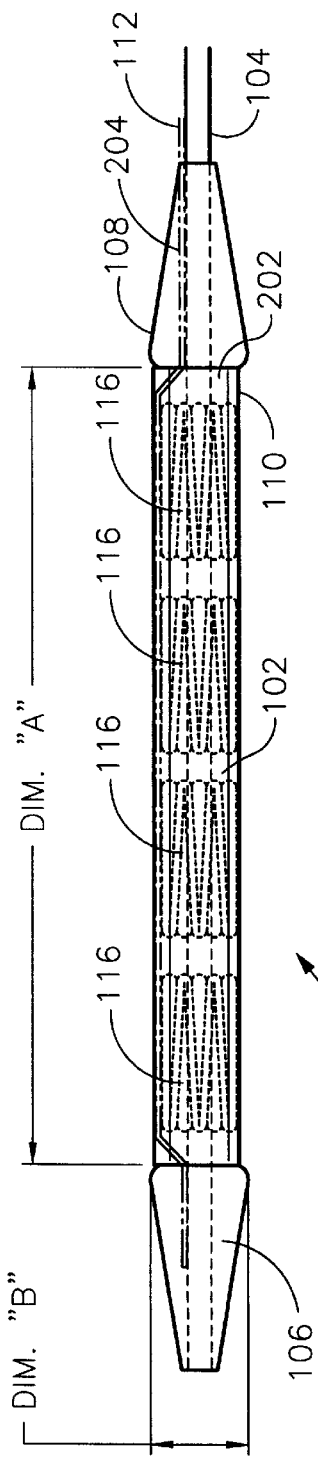
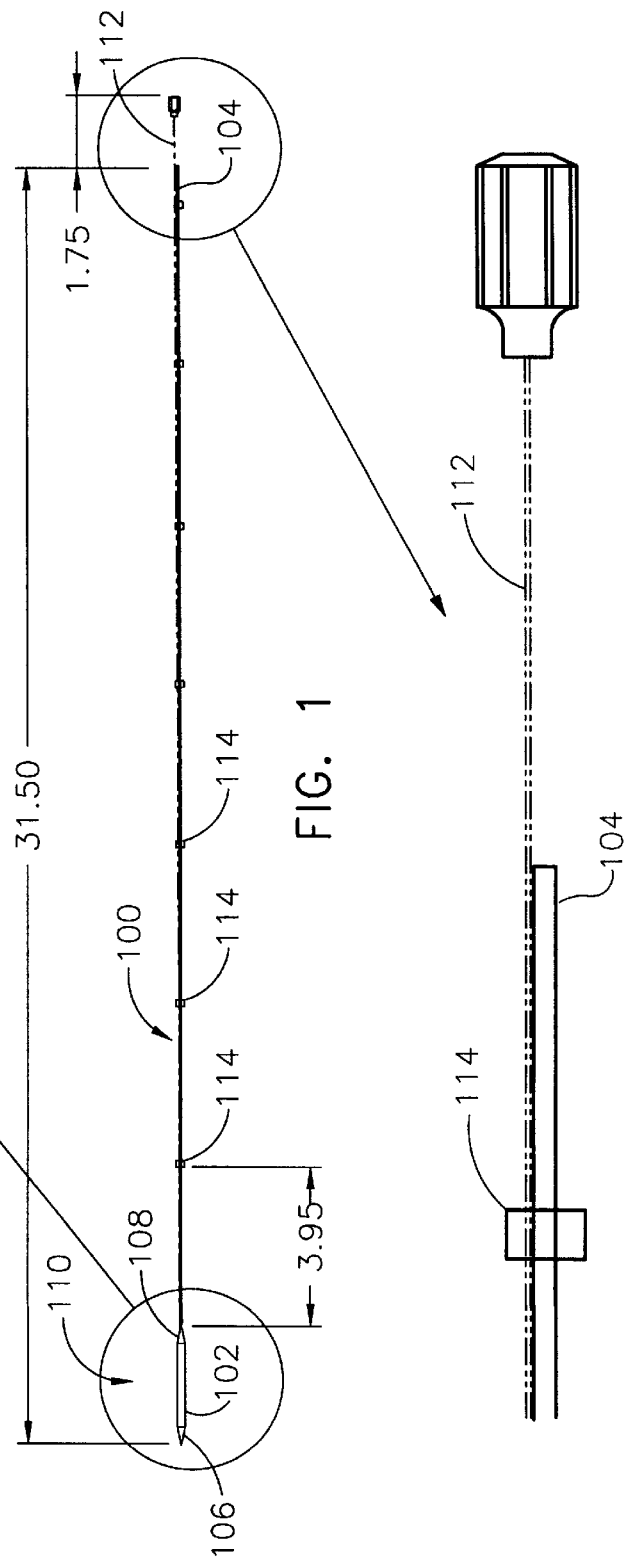
FIG. 1
FIG. 2

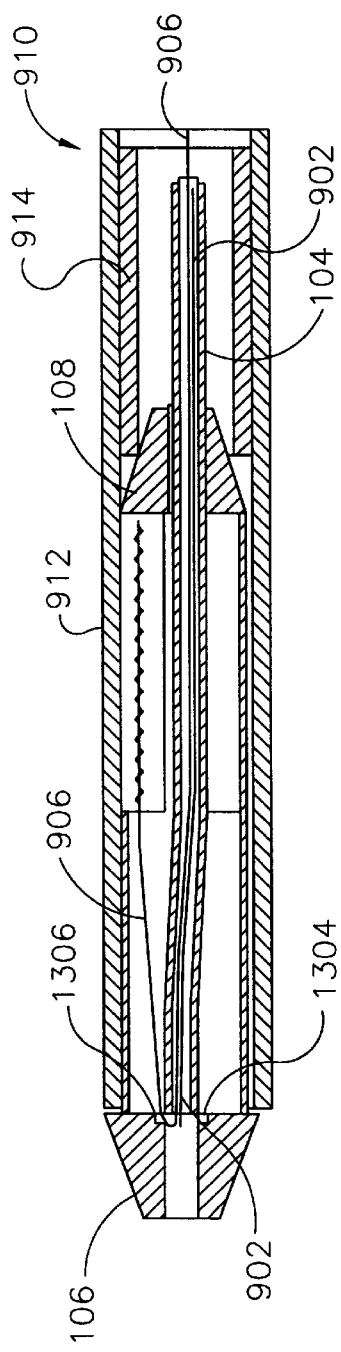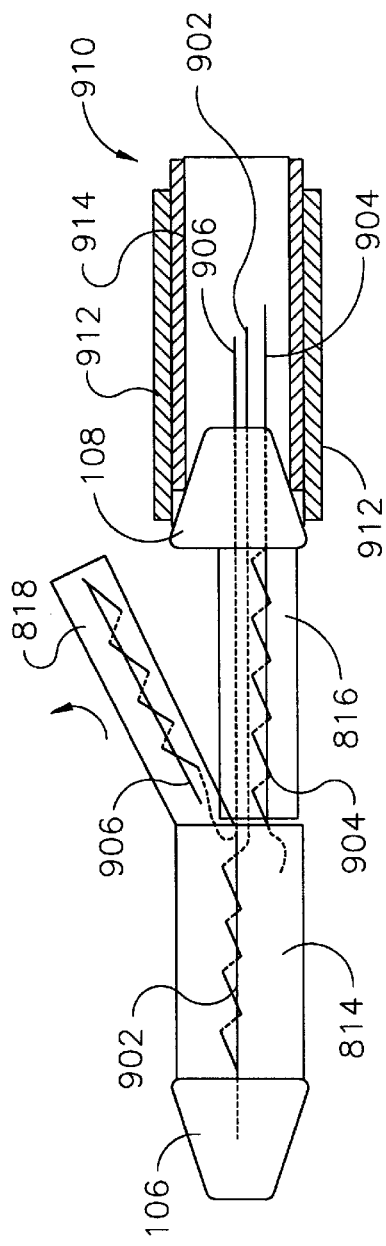
FIG. 12
FIG. 14

DELIVERY SYSTEM FOR SELF-EXPANDING STENTS AND GRAFTS

BACKGROUND OF THE INVENTION

The present invention relates to medical devices and procedures. More particularly, the present invention relates to a method and apparatus for percutaneous introduction of an endoluminal stent or stent graft that is particularly suited for percutaneous delivery of bifurcated stents or stent grafts into the vascular system of a patient.

Transluminal prostheses for implantation in blood vessels, biliary ducts, or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass occluded or damaged natural blood vessels. Examples of prosthetic vascular grafts are described in U.S. Pat. No. 4,955,899 (issued to Della Coma, et al. on Sep. 11, 1990); U.S. Pat. No. 5,152,782 (Kowligi, et. al., Oct. 6, 1992).

A form of transluminal prostheses, used to maintain, open, or dilate tubular structures or to support tubular structures, is commonly known as a stent, or when covered or lined with biocompatible material, as a stent-graft or endoluminal graft. In general, the use of stents, and stent-grafts for treatment or isolation of vascular aneurysms and vessel walls which have been thinned or thickened by disease (endoluminal repair or exclusion) are well known.

Many stents and stent grafts, are "self-expanding", i.e., inserted into the vascular system in a compressed or contracted state, and permitted to expand upon removal of a restraint. Self-expanding stents typically employ a wire of suitable material, such as a stainless steel, configured (e.g. bent) to provide an outward radial force, and/or formed of shape memory wire such as nitinol (nickel-titanium) wire. When the shape memory wire is employed, the stent is typically of a tubular configuration of a slightly greater diameter than the diameter of the lumen, e.g., blood vessel, in which the stent is intended to be used. The stent may be annealed at an elevated temperature and then allowed to cool in air so that the shape memory wire "remembers" the initial configuration. The shape memory wire is suitably martensitic at room temperature, austenitic at typical body temperature. For example type "M" nitinol wire is martensitic at temperatures below about 13° C. and is austenitic at temperatures above about 25° C.; type "M" wire will be austenitic at body temperature of 37° C. Such nitinol wire is "super elastic" in its austenitic state; the radial outward force exerted by the stent on the wall of the lumen, (e.g., blood vessel) is therefore substantially constant irrespective of the diameter of the vessel and the expanded stent.

Various forms of stents and/or stent grafts are described in U.S. Pat. Nos. 5,873,906 (issued to Lau, et. al. on Feb. 23, 1999); 5,302,317 (Kleshinski, et. al., May 11, 1999); 5,662,713 (Andersen, et. al., Sep. 2, 1997); 5,575,816 (Rudnick, et. al, Nov. 19th, 1996); 5,0507,767 (Maeda, et. al, Apr. 16th, 1996); 5,415,664 (Pinchuk, May 16, 1995); 4,655,771 (Wallsten, Apr. 7, 1987); 4,800,882 (Gianturco, Mar. 13, 1987); 4,907,336 (Gianturco, Sep. 9, 1988); and 5,718,724 (Goicoechea, Feb. 17, 1998).

In general, stents and stent grafts are deployed either by a "cut-down" procedure, i.e., cutting directly into the lumen from an entry point proximate to the site where the prosthesis is to be deployed, or through a less invasive percutaneous intraluminal delivery, i.e., cutting through the skin to access a lumen e.g., vasculature, at a convenient (minimally traumatic) entry point, and routing the stent graft through the lumen to the site where the prosthesis is to be deployed.

Intraluminal deployment is typically effected using a delivery catheter with coaxial inner (plunger) and outer (sheath) tubes arranged for relative axial movement. The stent is compressed and disposed within the distal end of the outer catheter tube in front of the inner tube. The catheter is then maneuvered, typically routed though a lumen (e.g., vessel), until the end of the catheter (and thus the stent) is positioned in the vicinity of the intended treatment site. The inner tube is then held stationary when the outer tube of the delivery catheter is withdrawn. The inner tube prevents the stent from being withdrawn with the outer tube, so that, as the outer tube is withdrawn, the stent radially expands into a substantially conforming surface contact with the interior of the lumen e.g., blood vessel wall. An example of such a delivery system is described in aforementioned U.S. Pat. No. 4,655,771 (Wallsten, Apr. 7, 1987).

Other more specialized forms of delivery systems are also used. For example, U.S. Pat. No. 5,415,664 issued to Pinchuk on May 16, 1995, describes a stent delivery and deployment apparatus including three concentric tubes: an interior hollow tube and an outer sheath (generally corresponding to the inner and outer tubes of the delivery system described above); and an inner tubular actuation member with a cup-like gripping member rigidly attached to the distal end thereof. Relative movement between the interior tube and the actuation member provides a selectively actuable clamping or gripping mechanism between the cup-like member and the end of the interior tube. The end of a stent or stent-graft is inserted into the cup-like member and clasped between the cup-like member and the end of the interior tube. The distal end of the introducer is inserted into the sheath and pulls the distal end of the stent into the sheath, thereby stretching and radially compressing the stent to a reduced diameter. The sheath containing the stent and the remainder of the introducer is maneuvered to the site for deployment of the stent. The introducer is held in a stationary position and the sheath is pulled partially back towards the proximal end of the introducer so that a middle portion of the stent is released from the sheath. The introducer, stent, and sheath can then be moved to precisely locate the stent before it is deployed. When the stent is in a precise desired location, the introducer is held in a stationary position and the sheath is pulled back further to release the proximal end of the stent. The distal end of the stent is then released from the cup-like cap member and the distal end of the hollow tube. The introducer is then removed through the lumen of the expanded stent.

Other devices for deploying self-expanding endoprosthesis are described in: U.S. Pat. No. 5,484,444 issued to Braunschweiler, et. al., on Jan. 16, 1996, (including a mechanism for recompressing and recapturing the endoprosthesis within an outer sheath to facilitate repositioning and extraction) and U.S. Pat. No. 5,833,694 (Poncet, Nov. 10, 1998) (including a mechanism for deploying multiple stents at multiple sites within a body passage without completely withdrawing any part of the deployment device from the patient's body); and 5,776,142 (Gunderson, Jul. 7, 1998) (including a mechanism for controlling axial movement of the ends of the stent towards each other while simultaneously controllably rotating the ends of the stent about the longitudinal axis to provide for its controlled radial expansion); and U.S. Pat. No. 5,700,269 (Pinchuk, et. al., Dec. 23, 1997) (including mechanism for retracting the stent).

The use of trigger or release wires to control expansion of self-expanding endoprosthesis are also known. For example, such a system is described in U.S. Pat. No. 5,019,085 issued to Hillstead on May 28, 1991. A stent is disposed on the exterior of the distal end of a catheter. An elongated wire is inserted down the catheter's passageway then routed outside the catheter through an opening in the catheter sidewall. The wire is then looped over the stent, and routed back into the catheter interior through a second opening in the catheter sidewall. The wire is routed through the catheter interior passageway to a third opening in the catheter sidewall where it is again routed outside the catheter's passageway to loop over a distal end of the stent. The wire is then inserted back into the catheter. The wire holds the stent compressed against the catheter wall as it is delivered to a desired position. When the stent is positioned at the desired deployment site, the stent is released by withdrawing the wire from the catheter a distance sufficient to free one end of the stent. The stent is then free to expand into an uncompressed state even though the wire still engages the stent at its proximal end. If in the physician's opinion, the stent has been properly positioned, continued withdrawal of the wire from the catheter completely frees the stent from the catheter and the catheter is withdrawn. If, however, the stent is improperly positioned, the wire can be held in place to retain the stent as both catheter and stent are withdrawn from the subject.

The aforementioned U.S. Pat. No. 5,873,906 to Lau, et. al., discloses another delivery system wherein a tether line is employed to maintain the stent or stent-graft in a folded configuration until release. The stent is deployed in a body lumen or cavity using a catheter comprising an interior tube (guide wire tubing) and an outer sliding sheath. The stent graft is placed between distal and proximal barriers fixed on the interior catheter (to hold the stent graft in axial position prior to deployment), with the catheter interior tube within the lumen of the stent graft. The stent or stent-graft is then, in effect, flattened and folded (wrapped) around the catheter inner tube. Two sets of loops are provided on the outer jacket of the stent graft, disposed so that they are in juxtaposition (in general linear alignment) when the stent graft is flattened and wrapped around the catheter. The tether wire is threaded through the respective sets of loops to hold the stent graft under compression i.e., folded, on the catheter. The tether wire is run through the exterior sheath of the catheter in parallel to interior tube. After the stent graft is placed in position, the tether wire is removed by sliding it axially along the stent and out of the loops so that the stent unfolds into a generally cylindrical shape within the body lumen or cavity.

The application of stent grafts to branched lumen (such as the infrarenal portion of the aortic artery where it bifurcates to the common iliac arteries) is also known. However, the deployment of a bifurcated stent is typically relatively invasive. For example, some bifurcated stents involve respective portions that are joined in situ and require a plurality of catheterizations are described in U.S. Pat. Nos. 5,916,263 (issued to Goicoechea, et al. on Jun. 29, 1999); 5,906,641 (Thompson, et. al., May 25, 1999); 5,695,517 (Marin, et. al., Dec. 9; 1997); 5,632,763 (Glastra, May 27, 1997); 5,609,627 (Goicoechea, et al., Mar. 11, 1997); and 5,316,023 (Palmaz, et. al., May 31, 1994).

It is also known to insert and advance a unitary bifurcated graft through a single branch of the femoral arterial system, to a point beyond the treatment site, then pull or draw one of the limbs into the contralateral (opposite) branch by significant and skillful manipulation of a contralateral-femoral wire catheter or snare. Such a system is described in U.S. Pat. No. 5,639,278 issued to Dereume, et. al., on Jun. 17, 1997. Other deployment systems require cross-femoral wire catheter and guidewires, such as described in U.S. Pat. No. 5,489,295 (Piplani, et. al., Feb. 6, 1996), and PCT Application WO 98/36708 (Endologix, published Aug. 27, 1998). In each case, catheterization in both femoral arteries is required.

It has also been suggested, U.S. Pat. No. 4,617,932 (Kornberg, Oct. 21, 1986), that blood flow entering the graft, can be utilized to cause the contralateral leg of a graft to float free in the blood stream so that it may be directed to the proper position.

Other stents for bifurcated lumen are deployed from the trunk (proximal) lumen e.g., the heart side of iliac arteries. Examples of such stents grafts are described in U.S. Pat. No. 5,906,640 issued to Penn, et. al., on May 25, 1999; U.S. Pat No. 5,755,734 issued to Richter, et. al., on May 26, 1998; U.S. Pat No. 5,827,320 issued to Richter, et. al., on Oct. 27, 1998. These devices, however, cause more trauma to the patient as they require large access ports in a portion of the vessel that is usually much deeper under the skin than the preferred femoral artery entry site.

Accordingly, there is a need for a deployment system that permits accurate placement of a stent graft without inordinate complexity, and for deploying bifurcated stents and stent grafts without requiring more than one catheterization. Further, it is desirable that the diameter of the compressed stent and insertion apparatus be as small as possible to facilitate insertion, particularly in smaller lumens, and to minimize trauma to the lumen. Accordingly, a stent that can be deployed without requiring the additional thickness of an external catheter would be desirable.

SUMMARY OF THE INVENTION

The present invention, in one aspect, provides a device for disposing a radially self-expanding endoprosthesis in a body lumen. The implanting device includes an elongated catheter having a distal end and an outer surface over which the endoprosthesis is placed, a sheath disposed to releasably surround at least a portion of the endoprosthesis, holding the endoprosthesis on the catheter in a radially contracted state, and a flexible elongation release element cooperating with the sheath. The sheath is released, permitting the surrounded portion of the endoprosthesis to expand, by axial withdrawal of the release element In one embodiment, a lead element is disposed on the outer surface of the catheter distally of the endoprosthesis and a follower element is disposed on the outer surface of the catheter proximally of the endoprosthesis to control axial movement of the prosthesis relative to the catheter. After the sheath is released and the prosthesis expands, the catheter (with lead and follower elements, if employed) is withdrawn. If desired, the sheath can be left within a body lumen; The outward radial force of the prosthesis captures and compresses the sheath between the prosthesis and the wall of the body lumen. Alternatively, a non-interfering attachment of the sheath to the catheter can be effected so that the sheath is withdrawn from the body lumen after deployment together with the catheter.

The present invention also, and another aspect, provides a particularly advantageous mechanism for deploying bifurcated endoprosthesis (including a main body and ipsilateral and contralateral legs). The distal end of catheter is passed through the interior passageway of the ipsilateral and leg, and the interior passageway of the main body. A first sheath is disposed to releasably surround the main body of endoprosthesis to hold the main body on the catheter in a radially contracted state. A second sheath is disposed to releasably surround the ipsilateral leg of the endoprosthesis to likewise hold the first leg on the catheter in a radially contracted state. A third sheath is disposed to releasably surround the second leg of the endoprosthesis, holding the second leg in a radially contracted state. A first elongated release element cooperates with at least the main body such that axial withdrawal thereof in the proximal direction releases the first sheath, permitting the main body of the endoprosthesis to expand. The first elongated release element can also cooperate with the ipsilateral leg, or a separate elongated release element can be employed, cooperating with the second sheath such that axial withdrawal thereof in the proximal direction releases the second sheath. A separate elongated release element cooperates with the third sheath, such that withdrawal thereof in the distal direction releases the third sheath, permitting the contralateral leg of the endoprosthesis to expand. The third elongated release element passes over the second sheath and extends toward the proximal end of the catheter.

BRIEF DESCRIPTION OF THE DRAWING

The preferred exemplary embodiment of the present invention will hereinafter be described in conjunction with the appended drawing, where like designations denote like elements, and:

FIG. 1 is a top view of an apparatus for introducing a self-expanding prosthesis in accordance with one aspect of the present invention;

FIG. 2 is a partially sectioned side view of the distal portion of the apparatus of FIG. 1;

FIG. 12 is a partially sectioned top view of the distal portion of an alternative embodiment of apparatus for introducing a bifurcated self expanding prosthesis in accordance with one aspect of the present invention;

FIG. 14 is a schematic top view of the apparatus of FIG. 9 with the contralateral leg of a bifurcated stent graft partially deployed;

DETAILED DESCRIPTION OF A PREFERRED EXEMPLARY EMBODIMENT

Figure 3A:
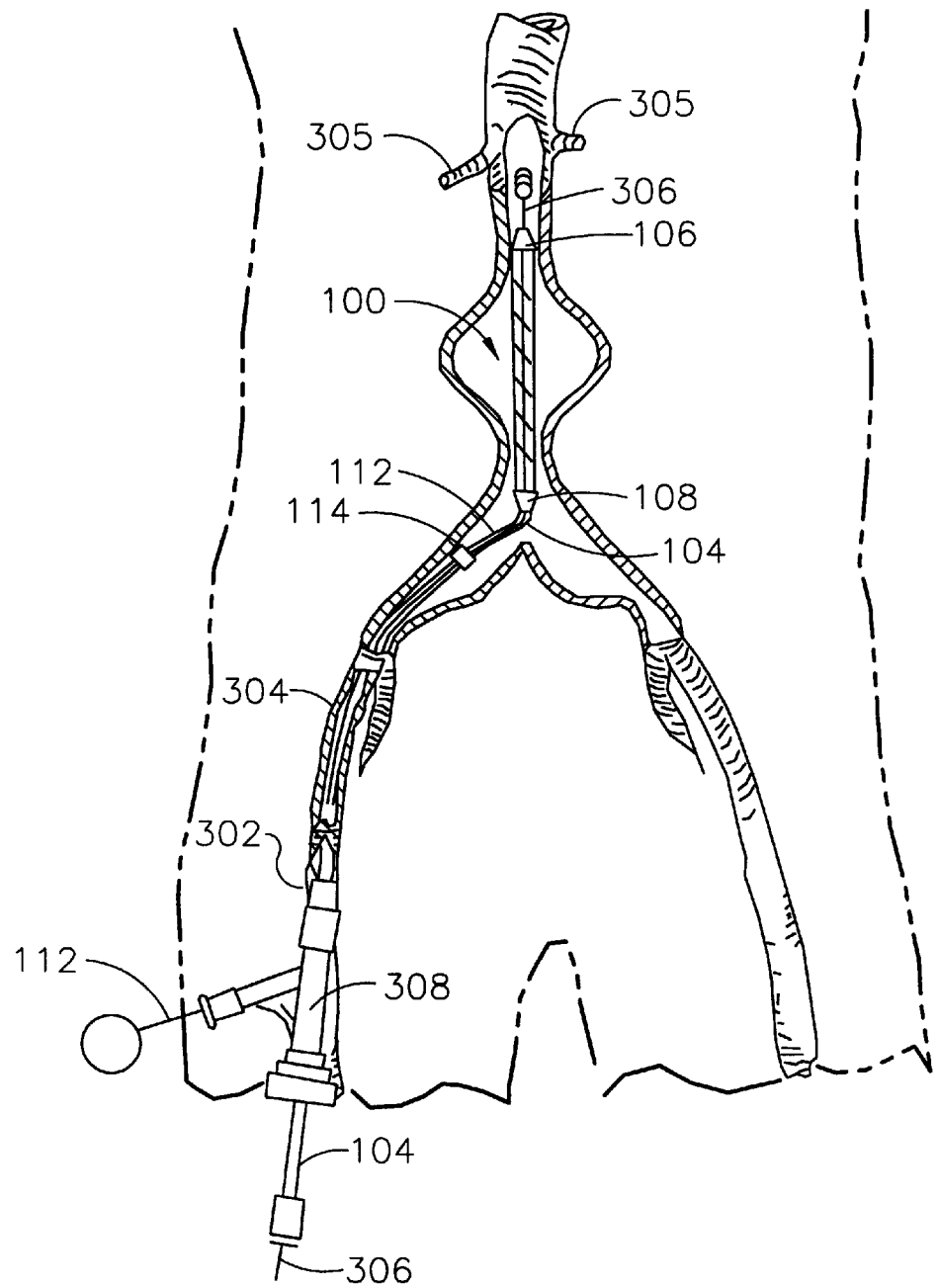
FIGS. 3A and 3B are schematic illustrations of the process of introducing self-expanding prosthesis employing the apparatus of FIG. 1.

Referring now to FIGS. 1–5, an introducer apparatus 100 for deploying a self expanding prosthesis 102 into a body lumen (e.g., blood vessel) suitably comprises: an elongated catheter 104, a sheath 110, a flexible elongated release element (e.g., release wire) 112, and, preferably, a lead element 106, a follower element 108, and respective retaining rings 114.

Figure 4:
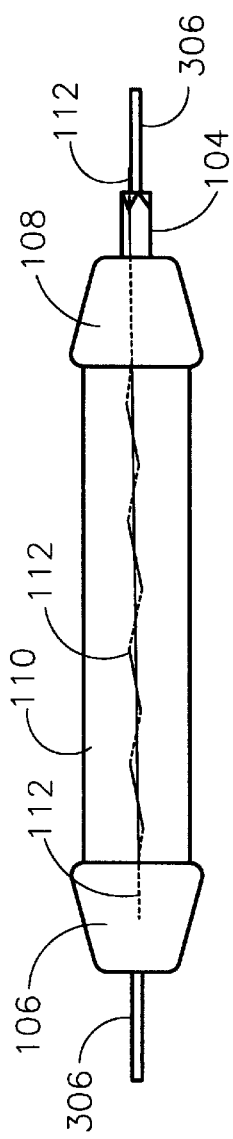
FIG. 4 is a top view of a stent graft disposed on the distal portion of the apparatus of FIG. 1.
Figure 5:
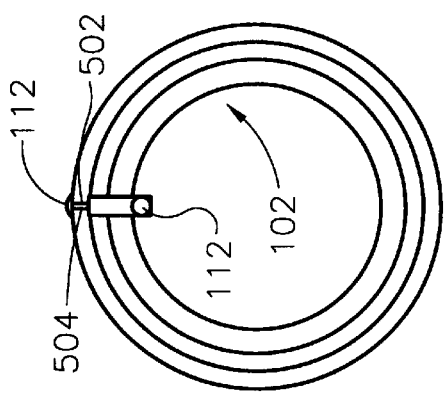
FIG. 5 is a partially sectioned side view of the lead element of the apparatus of FIG. 1.

As will be further discussed, prosthesis 102 is releasably disposed on the distal end of catheter 104 in a compressed state between lead element 106 and follower element 108 with catheter 104 passing through an internal lumen 202 (FIG. 2) of the prosthesis. Lead element 106 and follower element 108 fix the axial position of prosthesis 102 on catheter 104. Sheath 110, suitably a sheet of biocompatible material, e.g., PTFE, is disposed about (e.g., surrounding) at least a portion of prosthesis 102. As best seen in FIGS. 4 and 5, respective opposing edges 502 and 504 of sheath 110 are, releasably secured (e.g., pinned or bound) together by release element 112, maintaining prosthesis 102 in a compressed state. Release element 112 suitably passes through a passageway in follower element 108 and extends exteriorly of, and generally along, catheter 104 towards the proximal end of catheter 104. Referring again to FIGS. 1–5, retaining rings 114, if employed, provide relative position and between release element 112 and catheter 104.

In general, with specific reference to FIG. 3A, prosthesis 102 is deployed by puncturing the skin at a convenient (minimally traumatic) entry point 302, and entering a body lumen e.g., a blood vessel such as femoral artery 304, with a hollow needle (not shown). An elongated guide element (guide wire) 306 is typically passed into body lumen 304, extending into lumen 304 beyond the point at which prosthesis 102 is to be located, e.g., just below renal arteries 305 (the infrarenal portion of the aortic artery). Such guide wires tend to be relatively stiff, and facilitate control of the vessel and removal or lessening of sharp bends. The guidewire is typically employed to accommodate introduction of a variety of devices into the vessel such as, for example, an angiographic catheter, or balloon catheter.

A vessel dilator (not shown) is then suitably employed to expand entry point 302 and body lumen 304 to facilitate introduction of introducer 100. A hollow entry sheath 308 is then suitably introduced into body lumen 304 over guide wire 306 and the dilator removed. Entry sheath 308 is used to shutoff blood flow from the vessel with a valve.

Catheter 104 (with prosthesis 102 on the distal end thereof, and release element 112 running along the exterior thereof) is then inserted through entry sheath 308 and advanced along guide wire 306 (or otherwise maneuvered through lumen 304) to the site where prosthesis 102 is to be deployed. As will be explained, introducer 100 suitably travels directly within the interior of body lumen 304, without the necessity of an exterior catheter; entry sheath 308 need only extend through the skin into the vessel. Release element 112 extends outward from entry sheath 308, and is suitably terminated at its proximal end with a tab or pull ring 310.

Figure 3B:
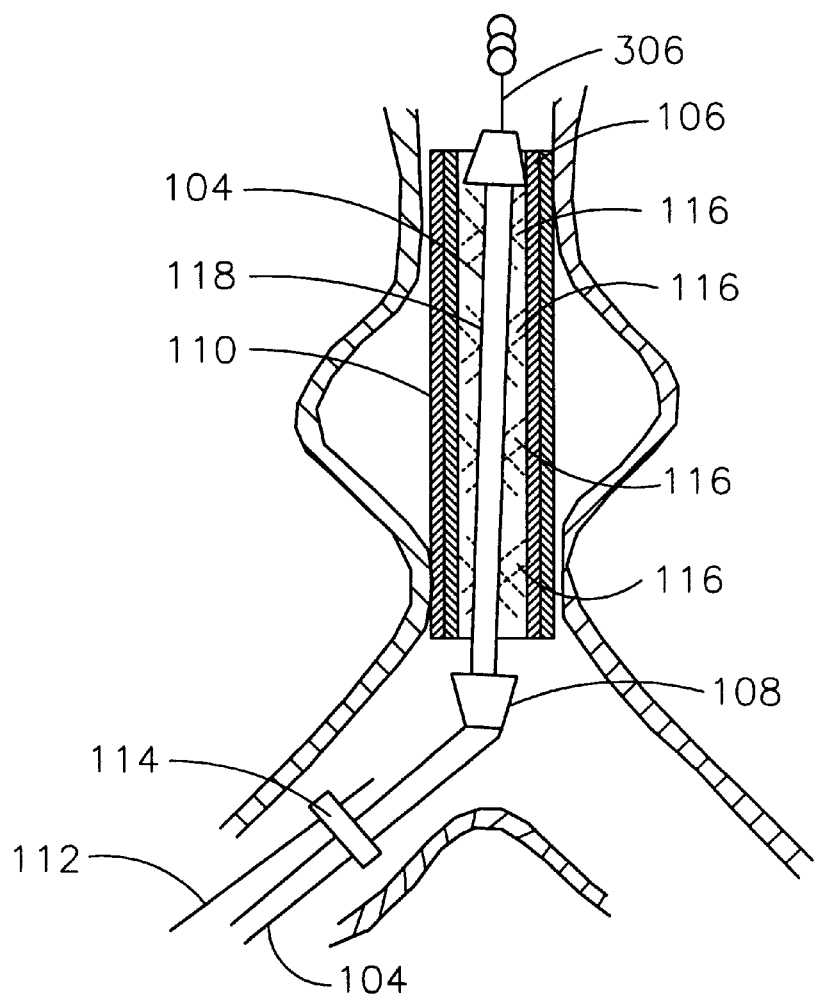

Referring to FIG. 3B, once prosthesis 102 is in position, release element 112 is pulled in the proximal direction and extracted, releasing sheath 110 so that prosthesis 102 expands. Introducer 100 may then be extracted by passing through the lumen of the expanded prosthesis, the interior of body lumen 304, and entry sheath 308. Sheath 110 may be left in the patient, held in place by the radial force of prosthesis 102 or extracted with introducer 100, if desired. If sheath 110 is to be extracted, an attachment to e.g., follower element 108 is effected in a manner that does not interfere with the expansion of prosthesis 102 upon release of sheath 110.

With reference to FIGS. 2 and 5, introducer 100 can accommodate substantially any manner of self expanding prosthesis 102, having an internal lumen 202, of a diameter sufficient to accommodate catheter 104 when in a compressed state, and to permit extraction of apparatus 100 when in an expanded state. Prosthesis 102 is suitably a stent-graft, including self-expanding stent portions 116, and a biocompatible cover 118. As will be discussed, introducer 100 is particularly suited for deploying bifurcated stent grafts.

Catheter 104 may comprise any flexible tubing suitable for intraluminal maneuvering of prosthesis 102 into a desired position within the body lumen. Catheter 104 is suitably of a predetermined outer diameter, (capable of being accommodated within prosthesis lumen 202 when prosthesis 102 is compressed), and includes an internal (preferably co-axial) lumen. As will be discussed in FIG. 3A, a suitable guide element (e.g., wire) 306 is typically received in the catheter lumen; the catheter slides along guide element to facilitate maneuvering prosthesis 102 into position.

Figure 6:
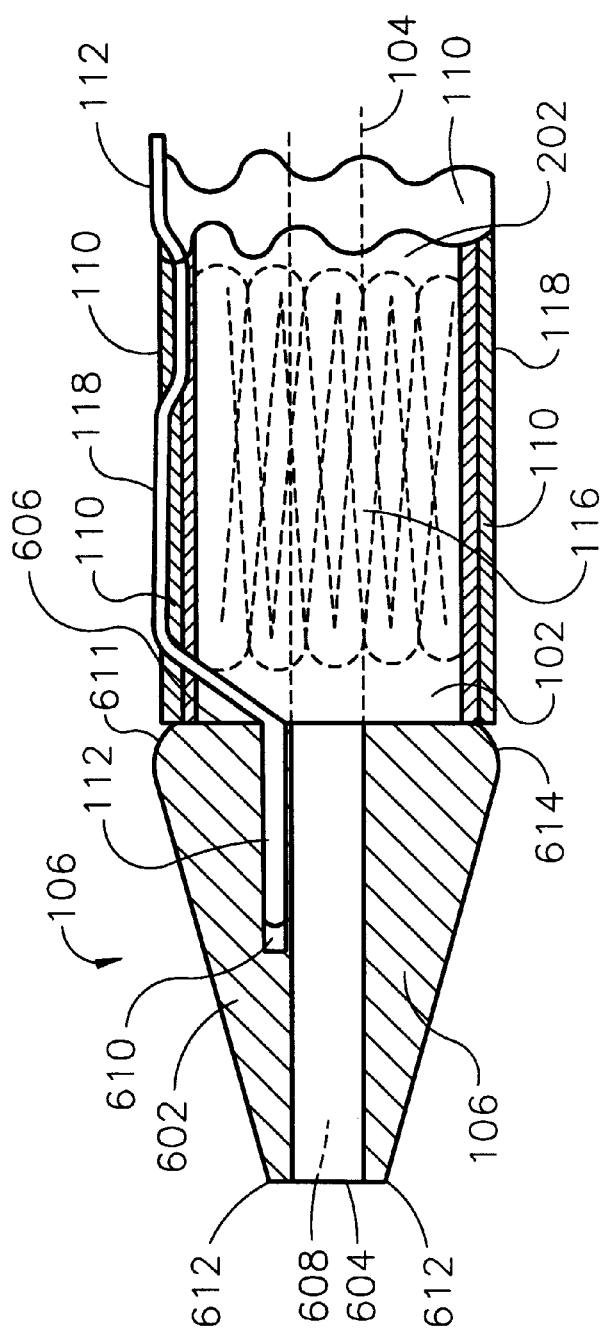
FIG. 6 is a front view of a stent graft maintained in a compressed state by the bound sheath of the apparatus of FIG. 1.

Lead element 106 and follower element 108 are employed to fix the axial position of prosthesis 102 on catheter 104 and are suitably configured to facilitate insertion and extraction of introducer 100 into and from body lumen 304. Lead element 106 also facilitates access and guiding of the catheter through lumens that are not always round and disease-free. Follower element 108 keeps the stent or stent graft in its axial position while the release wire is being removed. Elements 106 and 108 may be formed of any commonly known medical grade plastic, metal, or combination thereof and preferably is radio opaque. Referring to FIG. 6, lead element 106 suitably comprises a body 602, with a distal (front) end 604 and proximal end (base) 606, an axial through—bore 608, and, preferably, a retaining bore 610 adapted to receive the distal end of release element 112. Lead element 106 is suitably tapered in the distal direction, i.e., body 602 is suitably generally frustro-conical in shape, with rounded forward corners 612 to facilitate insertion. Distal end 604 is suitably of the diameter sufficient to comfortably slide through the appropriate size vessel entry sheath 308. Lead element 106 suitably also includes rounded rear edges 614 to facilitate extraction. The diameter of base 606 is suitably chosen to be just larger than the outer diameter of sheath 110, with prosthesis 102 maintained in a compressed state on catheter 104. The maximum diameter (e.g. rear edge 614) of lead element 602 suitably ranges in diameters from 5 French to 9 French for peripheral and coronary applications, and from 12 French to 24 French for iliac and aortic applications. Elements 106 and 108 may be attached to catheter 104 by compression fit, molding, or by any other commonly known bonding method.

Figure 7:
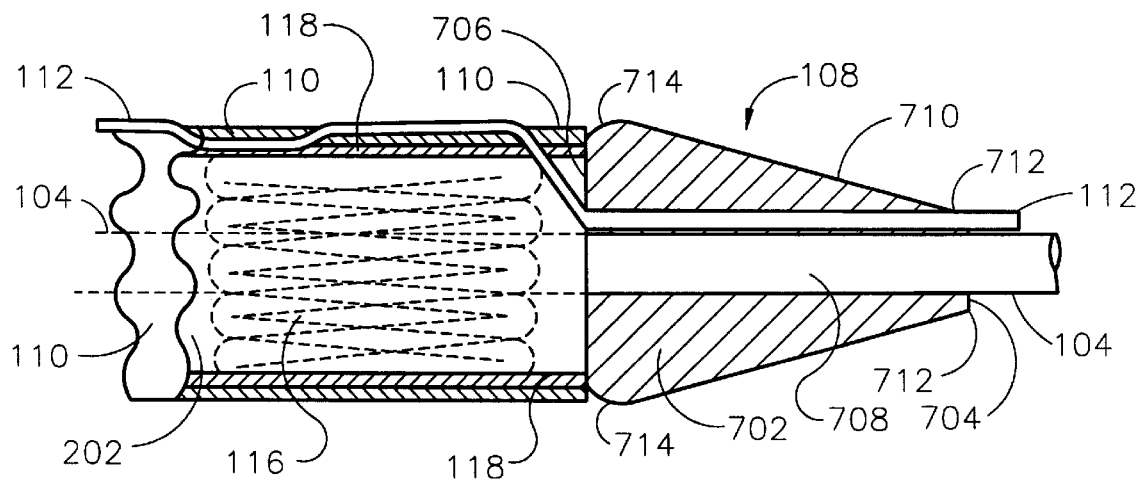
FIGS. 7 and 7A are partially sectioned side views of respective embodiments of the follower element of the apparatus of FIG. 1.

Referring now to FIG. 7, follower element 108 is suitably and substantially identical to lead element 106, but is reversed in direction on catheter 104, i.e., is tapered in the proximal direction to facilitate extraction, and includes a channel or passageway for accommodating passage of release element 112. Specifically, element 108 suitably comprises a body 702, with a proximal (small rear) end 704 and distal end (base) 706, an axial through—bore 708, and a channel or passageway 710 adapted to accommodate passage of release element 112. The peripheral edges 712 and 714 of follower element 108 and suitably rounded to facilitate extraction.

Figure 7A:
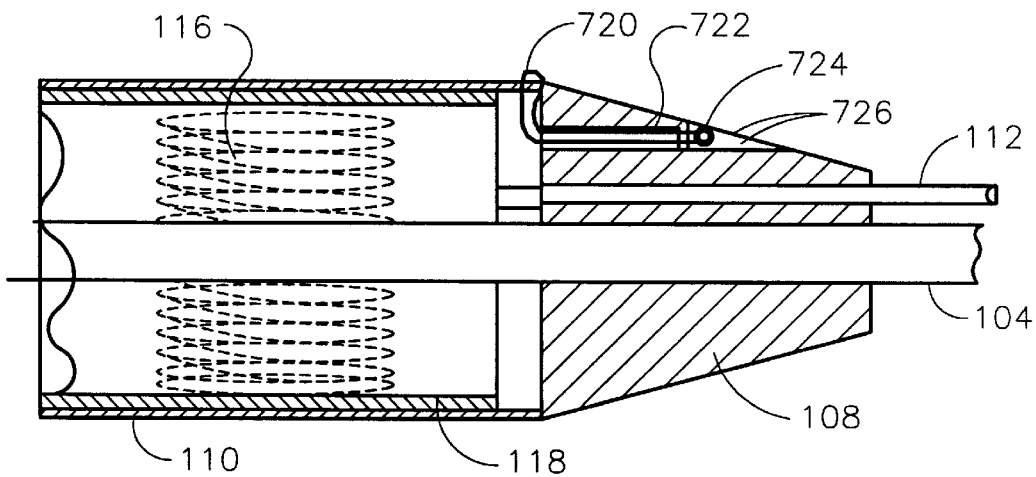
Figure 8:
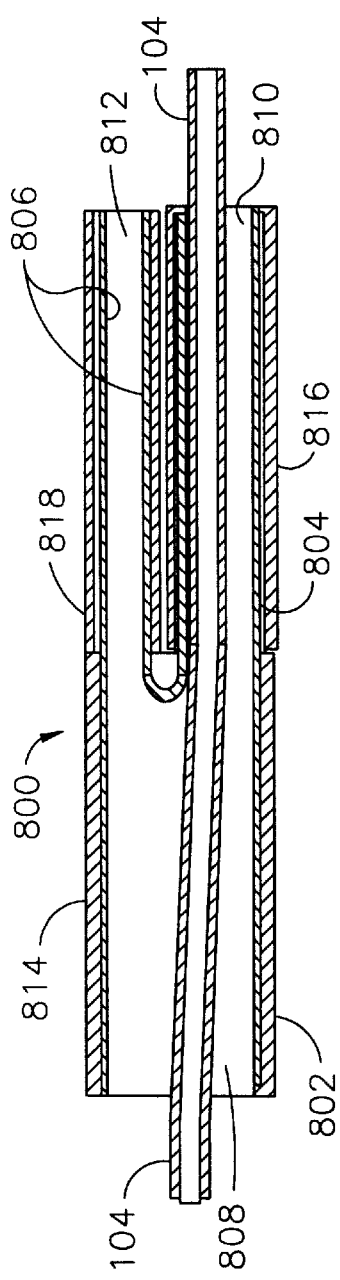
FIG. 8 is a sectional view of a bifurcated prosthesis, and cooperating sheaths.

If sheath 110 is to be extracted, an attachment to e.g., follower element 108 is effected in a manner that does not interfere with the expansion of prosthesis 102 upon release of sheath 110. For example, referring briefly to FIG. 7A, a suitable thread or wire 720 may be stitched through sheath 110 in the vicinity of the proximal edge of sheath 110, and fastened to a follower element 108 a suitable mechanism, e.g. passed through a channel 722 in follower element 108, through apertures in a suitable washer 724, and tied off (knot generally indicated as 726). Washer 724 and knot 726 are suitably disposed in a recess 728 in the sidewall of follower element 108 to facilitate extraction of apparatus 100 after deployment of prosthesis 102.

Sheath 110 is suitably formed of a sheet of relatively thin and flexible biocompatible material, such as PTFE, FEP, or a combination thereof, having a length corresponding to the length of the prosthesis, and a width bound by first and second opposing edges generally corresponding to the circumference of the compressed prosthesis. The material forming sheath 110 is suitably as thin as possible to provide a low profile, while still sufficiently strong to retain prosthesis 102 in its compressed state. For example, sheath 110 is suitably formed of laminated expanded PTFE of a thickness in the range of e.g., 0.002–0.01 in., and preferably 0.003 to 0.006 in.

As previously noted in FIG. 3A, introducer 100 suitably travels directly within the interior of body lumen 304, without the necessity of an exterior catheter. This is particularly advantageous in a number of respects: entry sheath 308 need only extend through the skin into the vessel, the profile of the overall device traversing the lumen is minimized, and the axial flexibility of the stent or stent graft is not compromised by an external sheath.

Introducer 100 is particularly suited for deploying multi-limbed prostheses, such as bifurcated stent grafts often employed in connection with treatment of the infrarenal portion of the aortic artery where it bifurcates to the common iliac arteries. The trunk and each limb of the prosthesis would employ a separate sheath, and release wire. Preferably, the release wire for the trunk and one leg would run in parallel in the axial direction. The release wire for the contralateral limb(s) would traverse the juncture bend so that they are, in effect, pulled from the front (distal direction) (rather than pulled from the rear (proximal direction) as in the case of the trunk and first leg). Such a procedure is particularly advantageous in that it requires only a single catheterization, and the trunk and respective legs can be released in any order.

Figure 9:
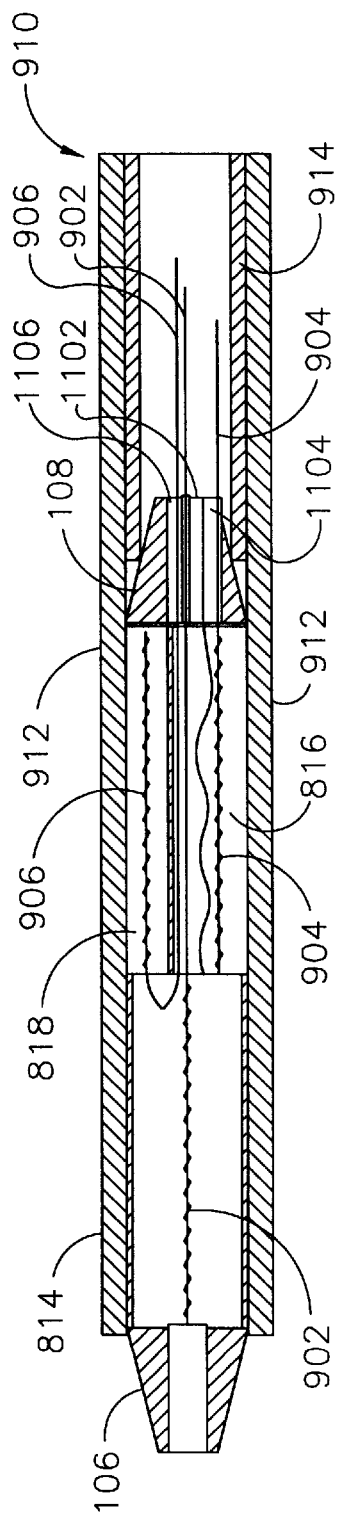
FIG. 9 is a partially sectioned top view of the distal portion of one embodiment of an apparatus for introducing a bifurcated self expanding prosthesis in accordance with one aspect of the present invention, with portions of the prosthesis removed for clarity.

More specifically, referring to FIGS. 8–11, a bifurcated stent graft 800 suitably comprises a main body 802, a first (ipsilateral) leg 804 and second (contralateral) leg 806, each including an interior passageway, 808, 810, and 812, respectively. Interior passageways 810 and 812 of the first and second legs 804 and 806 communicate with the interior passageway 808 of main body 802. A separate releasable sheath is provided for each portion of prosthesis 800 to maintain that portion of the prosthesis in a radially compressed state, e.g., a first sheath 814 is analogous to sheath 110, which is disposed about (e.g., surrounds) main body 802, a second sheath 816 surrounds leg 804, and a third sheath 818 surrounds leg 806. As best seen in FIG. 9, a separate release element is provided for each sheath: the respective opposing edges sheaths 814, 816, and 818 are pinned (threaded, bound) together to form respective tubes surrounding the associated portions of prosthesis 800 by an elongated release elements, e.g., wire, 902; 904; and 906. If desired, in some instances, release elements 902 and 904 can be combined as a single release element for both main body sheath 814 and sheath 816 for ipsilateral leg 804.

Intraluminal deployment is typically effected using a delivery catheter 910 suitably comprising an outer (sheath) tube 912 and coaxial inner (plunger) tube 914 arranged for relative axial movement. As will be discussed, prosthesis 800 (with sheaths 814, 816, and 818 in place) is compressed and disposed within the distal end of the outer catheter tube 912 in front of inner tube 914. In some instances, for example, when catheter 104 is sufficiently stiff to maintain the position of prosthesis 800 against the withdrawal of outer sheath 912, inner tube 914 may be omitted.

Figure 11:
FIG. 11 is a schematic illustration of the base of one embodiment of a follower element suitable for use in the apparatus of FIG. 9.

As best seen in FIGS. 9 and 11, suitable passageways 1102, 1104, 1106 and 1108 are provided in follower element 108 through which release elements 902–906 are journaled. Passageways 1102–1106 may open along one edge into axial bore 708, i.e., comprise channels molded or otherwise formed in the periphery of bore 708, or may comprise separate passageways.

The distal end of catheter 104 is passed through interior passageway 810 of ipsilateral leg 804, and interior passageway 808 of main body 802. Sheaths 814 and 816 thus hold main body 802 and ipsilateral leg 804 in a radially contracted state on catheter 104, and sheath 818 maintains contralateral leg 806 in a radially contracted state. As previously noted, prosthesis 800 (with sheaths 814, 816, and 818 in place) is compressed and disposed within the distal end of the outer catheter tube 912 in front of inner tube 914. Outer sheath 912 of delivery catheter 910 thus maintains contralateral leg 806 and sheath 818 compressed against ipsilateral leg 806 and catheter 104 until prosthesis 800 is deployed.

Release element 902, associated with main body 802, suitably approaches (enters) sheath 814 from the rear (proximal end), and extends toward the front (distal end), so that it is withdrawable in the proximal direction. Release element 902 extends from the rear (proximal end) of sheath 814, passes over sheath 816 (surrounding first leg 804 of endoprosthesis 800) through e.g., passageway 1102 in follower element 108 and extends the toward the proximal end of catheter 104.

Release element 904, associated with the ipsilateral leg 804, likewise suitably approaches (enters) sheath 814 from the rear (proximal end), and extends toward the front (distal end), so that it is withdrawable in the proximal direction. Release element 904 extends from the rear (proximal end) of sheath 814, passes through e.g., passageway 1104 in follower element 108 and toward the proximal end of catheter 104.

Release element 906, associated with contralateral leg 806, arranged to be withdrawn from sheath 818 in the distal direction, i.e., approaches sheath 818 from the front (distal end), and extends toward the rear (proximal end). Release element 906 extends from the front (distal end) of sheath 818 is routed across the juncture between the endoprosthesis legs, passes over sheath 816 (which surrounds first leg 804 of endoprosthesis 800) through passageway 1106 in follower element 108 and extends the toward the proximal end of the catheter.

With specific reference to FIG. 11, passageways through follower element 108 can be implemented in any conventional manner, including through bores and channels created by any of a number of well know methods including drilling, laser cutting, molding or EDM.

Figure 13:
FIG. 13 is a schematic illustration of the base of one embodiment of a lead element suitable for use in the apparatus of FIG. 12.

Referring now to FIGS. 12 and 13, if desired, one or more (e.g., all) of release wires 902–906 may approach their associated sheath from the front (distal end), and extend toward the rear (proximal end) of the sheath. In that case, the release wires would extend from the front (distal end) of the respective sheath to lead cone 106, then in a proximal direction through the interior of catheter 104. Lead cone 106 would suitably include grooves or passageways 1304–1308 to facilitate entry of the release wires into the interior of catheter 104.

Intraluminal deployment is typically effected using delivery catheter 910. As previously noted, prosthesis 800 (with sheaths 814, 816, and 818 in place) is compressed and disposed within the distal end of the outer catheter tube 912 in front of inner tube 914. Contralateral leg 806 and sheath 818 are thus compressed against ipsilateral leg 806 and catheter 104 until prosthesis 800 is deployed. Delivery catheter 910 is maneuvered, typically routed though a lumen (e.g., vessel), until the end of catheter 910 (and thus prosthesis 800) is positioned in the vicinity of the intended treatment site. Inner tube 914 is then held stationary and outer tube 912 is withdrawn. Inner tube 914 prevents prosthesis 800 from being withdrawn with outer tube 912, so that, as outer tube 912 is withdrawn, prosthesis 800 (with sheaths 814, 816, and 818 in place) is released with the interior of the lumen.

Figure 10:
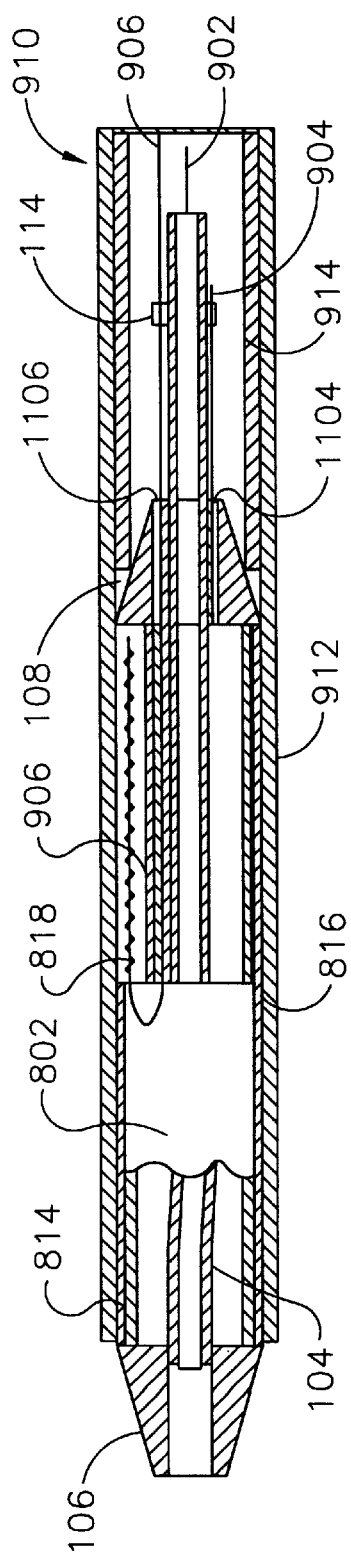
FIG. 10 is a partially sectioned top view of the apparatus of FIG. 9.
Figure 15:
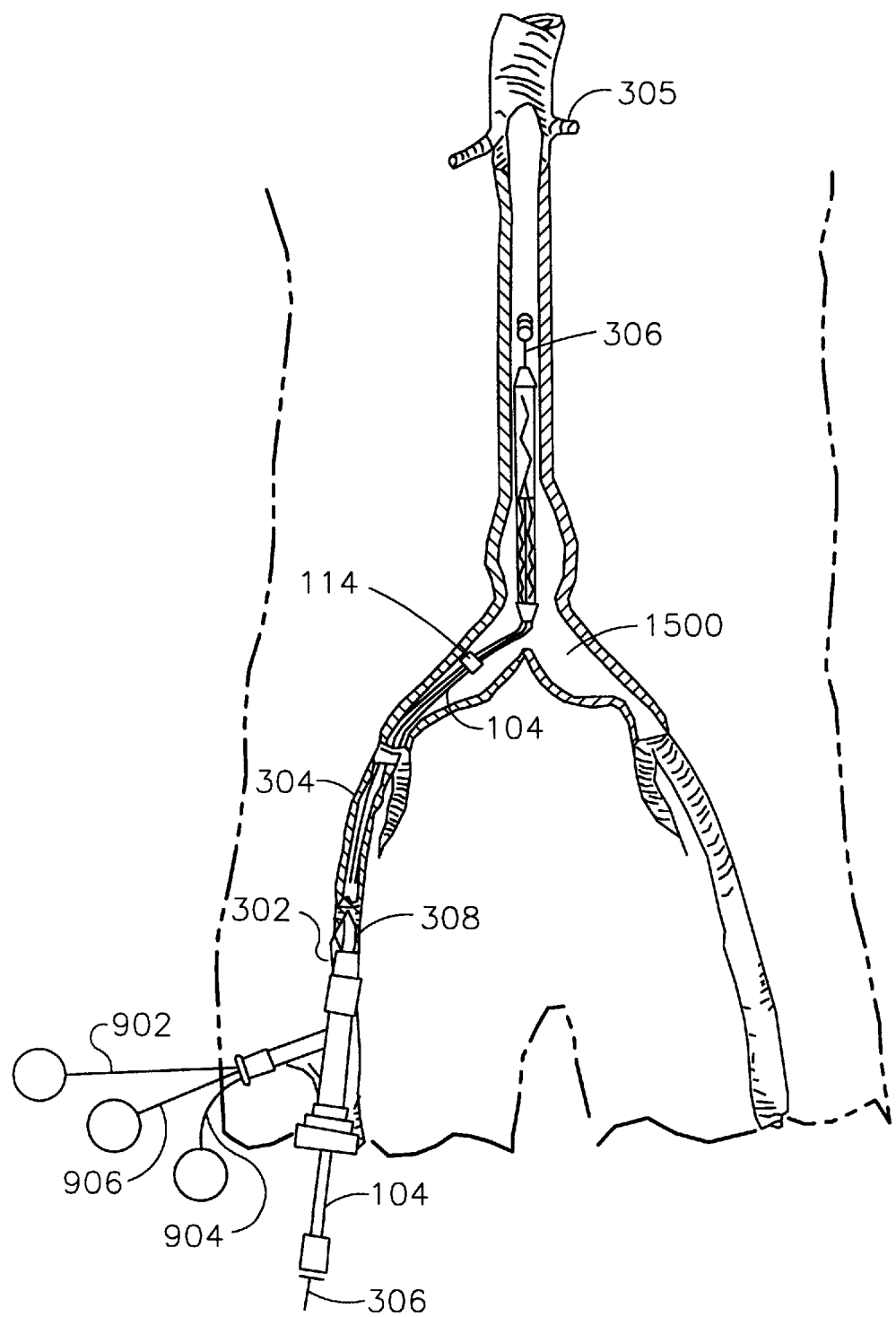
FIGS. 15–17 are schematic illustrations of the process of introducing a bifurcated self-expanding prosthesis.

More specifically, referring to FIGS. 9, 10, and 15, the subject's skin is punctured at entry point 302, to access a body lumen e.g., a blood vessel such as the femoral artery 304. The procedure is minimally invasive in that only a single puncture is required. As previously described, elongated guide element (guide wire) 306 is suitably passed into body lumen 304, extending into lumen 304 beyond the anatomical bifurcation (generally indicated as 1500) at which prosthesis 800 is to be located. Entry point 302 and body lumen 304 are suitably expanded with a vessel dilator (not shown) to facilitate introduction of introducer 100, entry sheath 308 introduced into body lumen 304 over guide wire 306 and the dilator removed.

As best seen in FIG. 15, delivery catheter 910 with prosthesis 800 disposed in the distal end thereof, and containing catheter 104 (and release elements 902, 904 and 906) is then inserted through entry sheath 308 and advanced along wire guide 306 (or otherwise maneuvered through lumen 304) to position prosthesis 800 at a point beyond anatomical bifurcation 1500. Delivery catheter 910, release elements 902, 904, and 906, interior catheter 104 and guide wire 306 all suitably extend outward from entry sheath 308.

Figure 16:
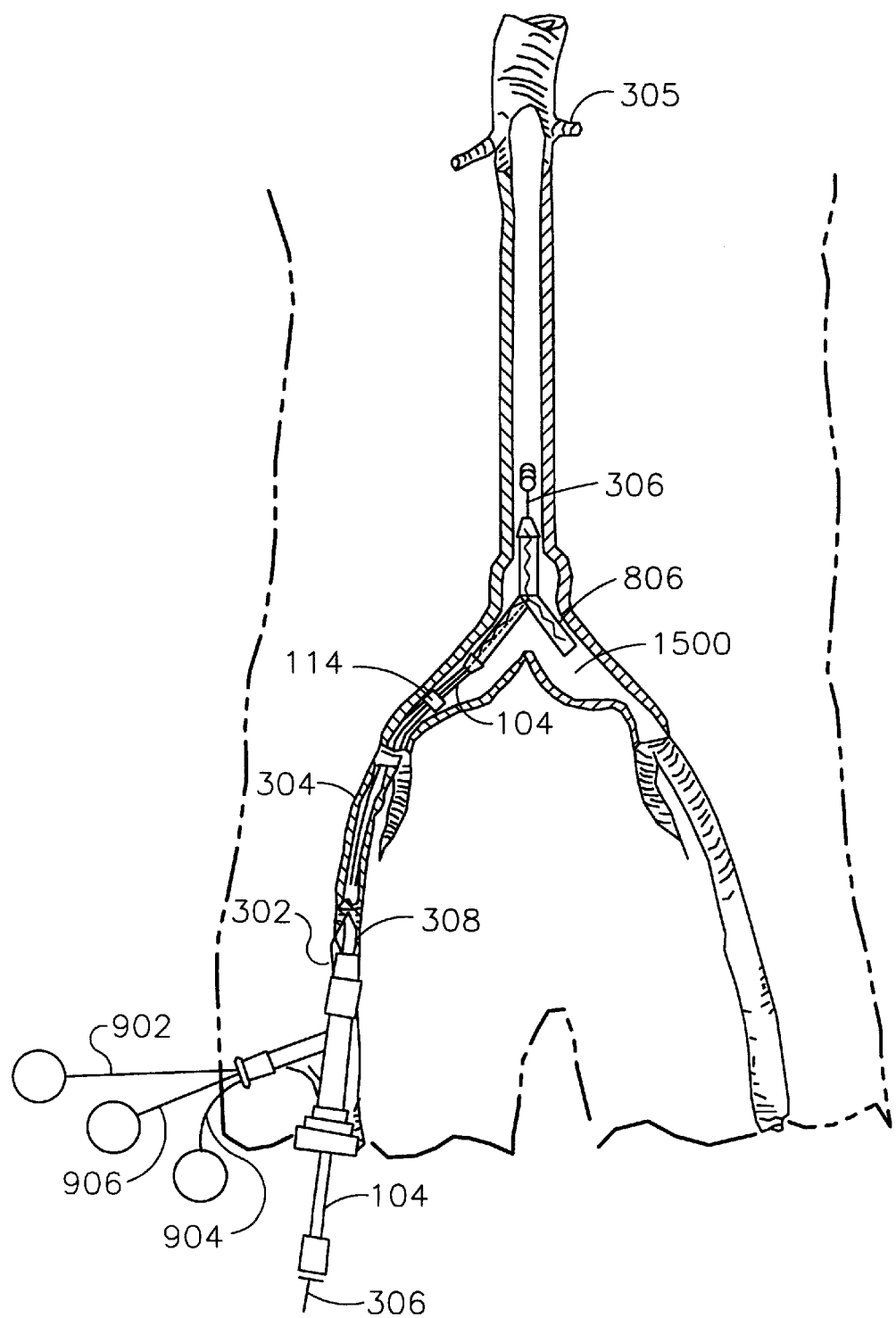

Referring to FIGS. 14 and 16, once prosthesis 800 is in position, outer tube 912 of delivery catheter 910 is withdrawn, with inner tube 914 held stationary such that prosthesis 800 is released into vessel 304. Contralateral leg 806 (still compressed by sheath 818) is thus released from ipsilateral leg 804 and catheter 104. When released from the compression of delivery catheter 910, contralateral leg 806 and sheath 818, in effect, expand, creating outward torque and, causing leg 806 (still compressed by sheath 818) to move transversely from ipsilateral leg 804 and catheter 104. Delivery catheter 910 may then be fully withdrawn, and discarded.

Figure 17:
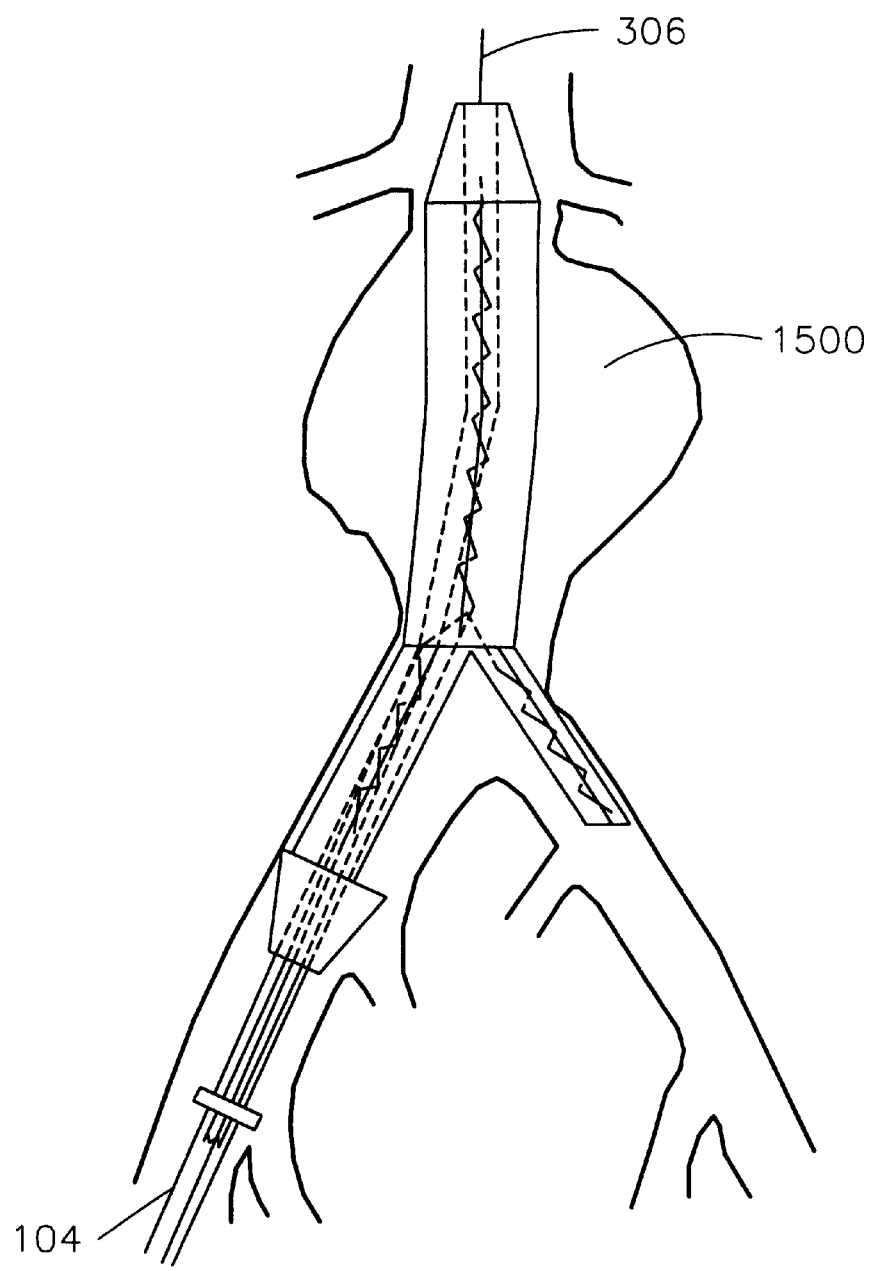

Referring to FIGS. 16 and 17, catheter 104 is then pulled back, causing prosthesis 800 to retreat along body lumen 304, such that contralateral leg 806 enters the contralateral branch of the body lumen from the aorta. Endoprosthesis 800 is suitably positioned with the main body 808 located where desired below (but not covering) renal arteries 305.

Once the trunk and both legs of prosthesis 800 are in position, release elements 902, 904, and 906 are pulled in the proximal direction and extracted, releasing sheaths 814, 816, and 818 so that body 802 and legs 804 and 806 of prosthesis 800 expand into contact with the walls of the body lumen. Release elements 902, 904, and 906 can be extracted in whatever order is most appropriate in the particular deployment desired based on the vessel anatomy. Introducer 100 may then be extracted, passing through the lumen of the expanded body 802 and ipsilateral leg 804 of prosthesis 800, the interior of body lumen 304, and entry sheath 308. Sheaths 814, 816, and 818 may be left in the patient, held in place by the radial force of prosthesis 800 or extracted with introducer 100, as desired. If one or more of sheaths 814, 816, and 818 is to be extracted, an attachment to e.g., follower element 108 is effected in a manner that does not interfere with the expansion of prosthesis 800 upon release of the sheath by providing capture wires that are attached to one corner of each of sheaths 814, 816, and 818. These wires may simply be pulled, after its corresponding release wire has been pulled, to slide the sheath around the deployed stent or stent graft and remove it through the vessel entry sheath 308.

The foregoing is a description of preferred exemplary embodiments and best mode of the invention known to the applicant at the time of filing the application. The invention is not limited to the specific forms shown. For example, modifications may be made in the design and arrangement of the elements within the scope of the invention, as expressed in the appended claims.

What is claimed is:

1. In combination, a radially self-expanding endoprosthesis, and an implanting device therefor comprising:
   an elongated catheter having a distal end and an outer surface over which said endoprosthesis is placed;
   at least a first sheath disposed to releasably surround at least a portion of the endoprosthesis to hold the endoprosthesis on the catheter in a radially contracted state; and
   a first flexible elongated release element cooperating with the first sheath, such that axial withdrawal thereof releases the first sheath, permitting the surrounded portion of the endoprosthesis to expand.

2. The combination of claim 1 further comprising a lead element disposed on the outer surface of the catheter distally of the endoprosthesis and a follower element disposed on the outer surface of the catheter proximally of the endoprosthesis to control axial movement of the prosthesis relative to the catheter.

3. The combination of claim 1 wherein:
   the endoprosthesis comprises a main body and ipsilateral and contralateral legs, each including interior passageway, the interior passageways of the ipsilateral and contralateral legs communicating with the interior passageway of the main body;
   the distal end of catheter is passed through the interior passageway of the ipsilateral leg, and the interior passageway of the main body;
   the first sheath is disposed to releasably surround at least the main body of endoprosthesis, to hold the main body on the catheter in a radially contracted state;
   the combination further comprises a second sheath disposed to releasably surround the contralateral leg of the endoprosthesis, holding the contralateral leg in a radially contracted state, and a second flexible elongated release element;
   the first elongated release element cooperates with at least the first sheath, such that axial withdrawal thereof in the proximal direction releases the first sheath, permitting the main body of the endoprosthesis to expand; and
   the second elongated release element cooperates with the second sheath, such that withdrawal thereof in the distal direction releases the second sheath, permitting the contralateral leg of the endoprosthesis to expand; the second elongated release element passing over the ipsilateral leg and extending toward the proximal end of the catheter.

4. The combination of claim 3 further comprising a third sheath is disposed to releasably surround the ipsilateral leg of the endoprosthesis to hold the ipsilateral leg on the catheter in a radially contracted state; and
   the second elongated release element passes over the third sheath along the ipsilateral leg of the endoprosthesis, extending toward the proximal end of the catheter.

5. The combination of claim 4 wherein the first elongated release element cooperates third sheath, such that axial withdrawal thereof in the proximal direction releases the third sheath, permitting the ipsilateral leg of the endoprosthesis to expand.

6. The combination of claim 4 further comprising a third elongated release element cooperating with the third sheath, such that axial withdrawal thereof in the proximal direction releases the third sheath, permitting the ipsilateral leg of the endoprosthesis to expand.

7. The combination of claim 6 wherein the first elongated release element passes over the second sheath along the ipsilateral leg of the endoprosthesis, extending toward the proximal end of the catheter.

8. The combination of claim 3 further comprising a delivery catheter in which the endoprosthesis and sheaths are received.

9. Apparatus for introducing a compressed self expanding prosthesis having an internal lumen in a body vessel in which an elongated guide element has been disposed, the apparatus comprising:
   an elongated catheter having a first predetermined outer diameter, a distal end, and an internal lumen, adapted to receive the guide element therethrough such that the catheter can slide along the guide element;
   a lead element, having an axial bore therethrough, fixedly disposed at the distal end of the catheter, in axial alignment therewith, the axial bore being adapted to receive the guide element therethrough;
   a follower element, having an axial bore and a passageway therethrough, disposed with the catheter passing through the axial bore, axially displaced from the lead element by a predetermined distance corresponding to the length of the prosthesis;
   the self-expanding prosthesis being received on the catheter between the lead and follower elements, with the catheter passing through the internal lumen of the prosthesis;
   a first sheath, formed of a sheet of relatively thin biocompatible material having a length corresponding to the length of the prosthesis, and a width, bounded by first and second opposing edges generally corresponding to the circumference of the compressed prosthesis;
   the first sheath being disposed about the compressed prosthesis; and an elongated release element, releasably binding the first sheath first and second opposing edges together, such that the sheath controllably maintains the prosthesis in a compressed state on the catheter between the lead and follower elements, the release element extending exteriorly of, and generally along, the catheter;

the release element releasing the sheath first and second opposing edges in response to being pulled in an axial direction, permitting the prosthesis to expand.

10. The apparatus of claim 9 for introducing an endoprosthesis comprising a main body and ipsilateral and contralateral legs, each including interior passageway, the interior passageways of the ipsilateral and contralateral legs communicating with the interior passageway of the main body, wherein:

the apparatus further comprises at least a second sheath, and second flexible elongated release element;

the distal end of the catheter is passed through the interior lumen of the ipsilateral leg, and the interior lumen of the main body;

the first sheath is disposed to releasably surround at least the main body of endoprosthesis to hold the main body on the catheter in a radially contracted state;

second sheath is disposed to releasably surround the contralateral leg of the endoprosthesis, holding the contralateral leg in a radially contracted state;

the first elongated release element cooperates with at least the first sheath, such that axial withdrawal thereof in the proximal direction releases the first sheath, permitting the main body of the endoprosthesis to expand;

the second elongated release element cooperates with the second sheath, such that withdrawal thereof in the distal direction releases the second sheath, permitting the contralateral leg of the endoprosthesis to expand; the second elongated release element passing over the ipsilateral leg and extending toward the proximal end of the catheter.

11. The apparatus of claim 10 further comprising a third sheath is disposed to releasably surround the ipsilateral leg of the endoprosthesis to hold the ipsilateral leg on the catheter in a radially contracted state; and the second elongated release element passes over the third sheath along the ipsilateral leg of the endoprosthesis, extending toward the proximal end of the catheter.

12. The apparatus of claim 11 wherein the first elongated release element cooperates third sheath, such that axial withdrawal thereof in the proximal direction releases the third sheath, permitting the ipsilateral leg of the endoprosthesis to expand.

13. The apparatus of claim 11 further comprising a third elongated release element cooperating with the third sheath, such that axial withdrawal thereof in the proximal direction releases the third sheath, permitting the ipsilateral leg of the endoprosthesis to expand.

14. The apparatus of claim 13 wherein the first elongated release element passes over the second sheath along the ipsilateral leg of the endoprosthesis, extending toward the proximal end of the catheter.

15. The apparatus of claim 9 further comprising a delivery catheter in which the endoprosthesis and sheaths are received.

16. A method for placing a self expanding prosthesis having an interior lumen within a body lumen comprising the steps of:

(a) mounting the prosthesis on one end of an elongated catheter by (i) disposing the end of the catheter within the prosthesis lumen; and (ii) disposing the prosthesis, in a compressed state, within a sheath formed of a sheet of biocompatible material with respective edges thereof releasably secured together by an elongated release element extending exteriorly of the catheter;

(b) inserting the elongated catheter into the body lumen to move the prosthesis to a placement position; and (c) with the prosthesis in position, maintaining the catheter substantially stationary, and withdrawing the elongated release element to release the sheath, permitting the prosthesis to expand, the outward radial force of the prosthesis capturing and compressing the sheath between the prosthesis and the wall of the body lumen; and (d) retracting the catheter from the body lumen.

17. The method of claim 16 further including the steps of effecting a non-interfering attachment of the sheath to the catheter, and withdrawing the sheath from the body lumen together with the catheter.

18. A minimally invasive method for deploying a self expanding bifurcated prosthesis within a bifurcated body lumen having ipsilateral and contralateral branches, through an entry point in the ipsilateral branch of the body lumen, the prosthesis comprising a main body and ipsilateral and contralateral legs, the method comprising the steps of:

(a) releasably surrounding the main body of the prosthesis with a first sheath of biocompatible material to controllably hold the main body in a radially contracted state, the first sheath being releasable from the entry point;

(b) releasably surrounding the ipsilateral leg of the prosthesis with a second sheath of biocompatible material to hold the ipsilateral leg in a radially contracted state, the second sheath being releasable from the entry point;

(c) releasably surrounding the contralateral leg of the prosthesis with a third sheath of biocompatible material to hold the contralateral leg in a radially contracted state, the third sheath being releasable from the entry point;

(d) disposing the prosthesis within the distal end of a delivery catheter, with the sheathed contralateral leg generally parallel to and compressed against the sheathed ipsilateral leg;

(e) inserting the delivery catheter through the entry point into the ipsilateral branch of the body lumen, and maneuvering the delivery catheter therethrough to position the prosthesis at a point in the body lumen beyond the juncture with the contralateral branch;

(f) displacing the prosthesis from the delivery catheter into the body lumen at a point in the body lumen beyond the juncture with the contralateral branch, the sheathed first and contralateral legs once released from the compression of the delivery catheter moving transversely apart;

(g) pulling the prosthesis in the direction of the entry point, to cause the sheathed contralateral leg to enter the contralateral branch of the body lumen; and (h) releasing the first, second, and third sheaths such that the main body and first and contralateral legs of the prosthesis expand against the walls of the body lumen.

19. The method of claim 18 wherein the surrounding steps (a), (b) and (c) each comprise disposing a portion of the prosthesis, in a compressed state, within a sheath formed of a sheet of biocompatible material with respective edges thereof releasably secured together by an elongated release element.

20. The method of claim 19 wherein the releasing step (h) further includes the step of capturing and compressing the sheaths between the prosthesis and the wall of the body lumen.

21. The method of claim 19 wherein:

at least the first sheath is releasably secured by a first elongated release element, withdrawable from the first sheath in the proximal direction, which extends toward the proximal end of the delivery catheter, and the releasing step (h) includes the step of axially withdrawing the first elongated element from the entry point; and the third sheath is releasably secured by a further elongated release element withdrawable from the third sheath in the distal direction; the further elongated release element passing along the ipsilateral leg of the endoprosthesis and extending toward the proximal end of the catheter, and the releasing step (h) includes the step of axially withdrawing the third elongated element from the entry point.

22. The method of claim 19 wherein:

the first sheath is releasably secured by a first elongated release element, withdrawable from the first sheath in the proximal direction, which passes over the second sheath along the ipsilateral leg of the prosthesis and extends toward the proximal end of the delivery catheter, and the releasing step (h) includes the step of axially withdrawing the first elongated element from the entry point;

the second sheath is releasably secured by a second elongated release element withdrawable from the second sheath in the proximal direction, which extends toward the proximal end of the delivery catheter, and the releasing step (h) includes the step of axially withdrawing the second elongated element from the entry point; and the third sheath is releasably secured by a third elongated release element withdrawable from the third sheath in the distal direction; the third elongated release element passing over the second sheath along the ipsilateral leg of the endoprosthesis and extending toward the proximal end of the catheter, and the releasing step (h) includes the step of axially withdrawing the third elongated element from the entry point.

23. The method of claim 18 wherein the main body and each leg of the prosthesis includes an interior lumen, with the interior lumens of the first and contralateral legs communicating with the interior lumen of the main body, further including the steps of:

prior to surrounding steps (a), (b) and (c) passing the distal end of an interior catheter through the interior lumen of the ipsilateral leg, and the interior lumen of the main body such that surrounding steps (a) and (b) hold the main body and ipsilateral leg of the prosthesis on the interior catheter in a radially contracted state until the sheaths are released.

* * * * *